US010845615B2

(12) United States Patent
Thorsteinsson

(10) Patent No.: US 10,845,615 B2
(45) Date of Patent: Nov. 24, 2020

(54) METHOD OF GENERATING A THREE DIMENSIONAL SURFACE PROFILE OF A FOOD OBJECT

(71) Applicant: MAREL ICELAND EHF, Gardabaer (IS)

(72) Inventor: Tómas Thorsteinsson, Kopavogi (IS)

(73) Assignee: MAREL ICELAND EHF, Gardabaer (IS)

( * ) Notice: Subject to any disclaimer, the term of this patent is extended or adjusted under 35 U.S.C. 154(b) by 0 days.

(21) Appl. No.: 16/337,553

(22) PCT Filed: Sep. 28, 2017

(86) PCT No.: PCT/EP2017/074612
§ 371 (c)(1),
(2) Date: Mar. 28, 2019

(87) PCT Pub. No.: WO2018/060325
PCT Pub. Date: Apr. 5, 2018

(65) Prior Publication Data
US 2020/0033616 A1    Jan. 30, 2020

(30) Foreign Application Priority Data

Sep. 29, 2016  (EP) .................... 16191452

(51) Int. Cl.
*G01N 23/06*   (2018.01)
*G02B 30/50*   (2020.01)
(Continued)

(52) U.S. Cl.
CPC .............. *G02B 30/50* (2020.01); *A61B 6/584* (2013.01); *G01B 15/025* (2013.01); *G01B 15/04* (2013.01); *G01G 9/005* (2013.01); *G01N 33/02* (2013.01)

(58) Field of Classification Search
CPC ......... A61B 6/584; A61B 6/032; A61B 1/045; A61B 1/24; A61B 2017/00057;
(Continued)

(56) References Cited

U.S. PATENT DOCUMENTS 5,585,603 A    12/1996  Vogeley, Jr.
6,449,334 B1 *  9/2002  Mazess ................ G01N 23/083
378/53

(Continued)

FOREIGN PATENT DOCUMENTS

EP    0170778 A1   2/1986
EP    2636495 A1   9/2013
(Continued)

OTHER PUBLICATIONS

International Search Report from PCT Application No. PCT/EP2017/074612, dated Nov. 15, 2017.
(Continued)

*Primary Examiner* — Irakli Kiknadze
(74) *Attorney, Agent, or Firm* — Workman Nydegger

(57) ABSTRACT

A method of generating a three dimensional surface profile of a food object is provided wherein a food object is exposed with a conical X-ray beam while the food object is conveyed. The attenuation of the X-rays after penetrating through the food object is detected, and the detection is performed using a plurality of sensors arranged below the food object. The plurality of sensors are positioned at predetermined angular positions in relation to the X-ray source. For each of the plurality of sensors, the detected attenuation is converted into a penetration length of the X-ray beam, and the penetration length indicates the length from where the X-ray beam enters and leaves the food
(Continued)

object. Surface coordinates are sequentially determined using the penetration lengths and the angular positions as input data.

10 Claims, 3 Drawing Sheets

(51) Int. Cl.
*A61B 6/00* (2006.01)
*G01B 15/02* (2006.01)
*G01B 15/04* (2006.01)
*G01G 9/00* (2006.01)
*G01N 33/02* (2006.01)

(58) Field of Classification Search
CPC ........ A61B 2034/101; A61B 2034/102; A61B 2034/105; A61B 2090/364; A61B 2090/373; A61B 2090/374; A61B 34/20; A61B 5/0071; A61B 5/0075; A61B 5/0077; A61B 5/0088; A61B 5/1077; A61B 5/4836; A61B 5/743; A61B 6/00; A61B 5/0507; A61B 2034/108; A61B 34/10; A61B 5/05; A61B 8/4245; G01B 15/025; G01B 15/04; G01B 15/045; G01B 11/22; G01G 9/005; G01N 33/02; G01N 33/12; G01N 21/8851; G01N 2201/10; G01N 2201/12; G01N 2223/419; G01N 23/046; G01N 23/083; G01N 23/18; G01N 23/04; G01N 23/087; G01N 15/082; G01N 2223/321; G01N 2223/3303; G01N 2223/41; G01N 2223/6126; G01N 2223/618; G01N 2223/639; G01N 2223/647; G01N 23/10; G01N 33/025; G01N 33/10; G01N 2223/206; H04N 5/247; G02B 30/50
USPC .................. 378/53, 54, 57, 58, 62, 98.2
See application file for complete search history.

(56) References Cited

U.S. PATENT DOCUMENTS

| 9,256,930 | B2* | 2/2016 | Suzuki | G01B 15/04 |
| 2004/0086076 | A1* | 5/2004 | Nagaoka | A61B 6/463 378/4 |
| 2017/0020478 | A1* | 1/2017 | Tanaka | A61B 6/032 |

FOREIGN PATENT DOCUMENTS

| EP | 2778662 A1 | 9/2014 |
| WO | 2008039056 A1 | 4/2008 |

OTHER PUBLICATIONS

European Search Report from EP Application No. 16191452, dated Dec. 1, 2016.
Jiménez et al., "Monte Carlo Simulation of an X-Ray System for Tomography Computerized Conical Beams (CBCT)", Latin America Journal of Medical Physics, vol. 2, No. 2, Apr. 2016, pp. 66-70.
Search Report from corresponding ES Patent Application No. 201900826, dated Aug. 6, 2020.
Search Report from corresponding Chilean Patent Application No. 201900826, dated Aug. 6, 2020.

* cited by examiner

METHOD OF GENERATING A THREE DIMENSIONAL SURFACE PROFILE OF A FOOD OBJECT

FIELD OF THE INVENTION

The present invention relates to a method of generating a three dimensional surface profile of a food object.

BACKGROUND OF THE INVENTION

U.S. Pat. No. 5,585,603 discloses a method and a system for weighing a food object as it is carried by a conveyor and moved past an X-ray source where it is exposed with a conical X-ray beam. The X-rays passing through the food object are attenuated relative to the mass of the food object, and impinge upon an X-ray detector array. The signal is processed and converted to a value representing the average areal density of the food object and thus the mass or mass map of the food object, which may be used for cutting the food object into portions.

X-rays that are emitted from an X-ray source (a point source) are by nature cone shaped. Due to this natural shape, they will diverge with increasing distance from the source. As a result, the signal produced by the X-ray detector array represents the average density of a wedge shaped slice, which introduces an error in the mass measurement and thus an error in the subsequent processing. A proposed solution (in U.S. Pat. No. 5,585,603) to partially overcome this problem is to move the X-ray source further away from the food object. This however results in a dramatic decrease in the power of the X-ray which is reflected in less clear image.

The above mentioned inaccuracy may be overcome by using a surface scan device such as a line laser device or similar means to obtain an accurate surface profile image of the food object. This however does not only require an additional surface scan device but also complicated software to generate the surface profile. Obviously, this solution will make the overall processing more complex and space demanding.

SUMMARY OF THE INVENTION

It would be advantageous to achieve an improved and simplified solution in obtaining a more accurate three dimensional (3D) surface, or density profile of a food object which may an important tool for subsequent processing steps of the food object.

In general, the invention preferably seeks to mitigate, alleviate or eliminate one or more of the above mentioned disadvantages singly or in any combination. In particular, it may be seen as an object of the present invention to provide a method for obtaining a surface profile of a food object that solves the above mentioned problems, or other problems, of the prior art.

To better address one or more of these concerns, in a first aspect of the invention a method is provided of generating a 3D surface profile of a food object, comprising:
exposing the food object with a conical X-ray beam while the food object is conveyed,
detecting the attenuation of the X-rays after penetrating through the food object, the detection being performed using a plurality of sensors arranged below the food object, the plurality of sensors being positioned at a pre-determined positions in relation to the X-ray source,
converting, for each of the plurality of sensors, the detected attenuation into a penetration length of the X-ray beam, the penetration length indicating the length from where the X-ray beam enters and leaves the food object, and
sequentially determining surface coordinates using the penetration lengths and the sensor positions as input data.

Accordingly, the surface coordinates provide input data necessary in generating a highly accurate 3D surface profiles of the food object, which may be adapted to be used as input for at least one subsequent processing step, e.g. in determining a highly accurate mass map of the food object to be used for accurate portioning.

Moreover, the surface coordinates and the penetration lengths provide sufficient information to make an appropriate correction of the attenuation of the cone shaped X-rays such that the attenuation corresponds to a vertical attenuation through the object. Thus, the error caused due to the natural cone shape X-ray beam is corrected while maintaining the power of the X-ray high since there is no need to move the X-ray source away from the food object. Accordingly, the accuracy in utilizing the X-ray attenuation in determining the weight of sub-parts of the food object may be improved.

The food object according to the present invention are considered to be essentially homogeneous materials, e.g. chicken, fish, meat, typically having density close to 1. Thus, the term "penetration length" may according to the present invention be understood or be equivalent to density, and thus the term 3D surface profile may according to the present invention also be understood or be equivalent as a 3D density profile.

The term positioning the sensors at a pre-determined positions in relation to the X-ray source may according to the invention be understood as a pre-determined angle positions, e.g. such that the sensor positioned directly below the X-ray source may be considered as being at a 0° angle position (corresponding to that an axis extending between this sensor and the source is vertical). The plurality of sensors may be sensor elements in an X-ray detection array.

In one embodiment, the detected attenuation of the X-rays after penetrating through the food object is also used in detecting e.g. bones or other undesired objects in the food object. The one or more subsequent processing step may be processing step(s) after the bones or other undesired objects have been detected, where this information is used as additional input data. The at least one processing step could include cutting the food object such that it fulfils at least one target criterion, e.g. a weight target and/or thickness target, with high accuracy resulting in high yield of the processing, using the 3D surface profile as input data.

The at least one processing step may also in one embodiment comprise a cutting process that is performed in accordance to the detected undesired object or bones.

In an embodiment, the detected undesired object or bones may further be used in operating the angle of the cutting in the food object. If the food object is e.g. a fish fillet and where the detected bones comprise the bone structure of the fish fillet, the cutting process may include cutting around the bone structure and simultaneously following the angle of the bones and thus increase the yield of the processing.

Based on the above, advantageously the detected attenuation of the X-rays may not only be used in detecting bones and any type of undesired objects, but also to generate the highly accurate 3D surface profile, meaning that no additional surface profile device such as a line scanner is needed. The whole processing obviously becomes more compact and economical.

The step of sequentially determining the surface coordinates may be done using well known geometrical calculations where the penetration length is detected using the sensor(s). Knowing this length and the angle position of the sensor(s) the surface coordinate where the X-ray(s) enter the food object may be calculated.

In one embodiment, the step of converting the detected attenuation into the penetration length is performed in accordance to a pre-calibration. Such a pre-calibration may e.g. be performed by exposing a number of food objects of the same type having different sizes/shapes with the X-ray and linking the detected attenuation of the X-rays to the actual penetration length of the food objects. As an example, if the food object is a uniform or substantially uniform material of e.g. particular type, e.g. such as a fish fillet, a large number of such fish fillets would be utilized for the pre-calibration. Another solution could be to expose a material having similar properties as the food object.

Another alternative to obtain the penetration length is to collect preferably a substantial amount of attenuation data for preferably identical type of food object, or material having similar material properties, and perform fitting based on the data. In that way, a detected attenuation value or a pixel value for a given sensor (may also be referred to as a pixel), can be fed into a formula produced by the fitting process which could convert it into the penetration length value.

In one embodiment, the plurality of sensors are arranged in at least one line perpendicular to a conveying direction of the food item. In an arrangement where there is a single line of sensors the three dimension surface profile will be based on plurality of two dimensional surface profiles accumulated together, whereas in case of two or more lines the sensors form an array of sensors and the three dimension surface profile will be based on plurality of three dimensional surface "slice" profiles.

As an example, an X-ray source exposes the food object 204 it's natural conical X-ray shaped beam while the food object is conveyed by a conveyor means. The X-rays passing through the food object are detected by the plurality of sensors.

Assuming a horizontal axis is an y-axis and a vertical axis is an z-axis, then a surface coordinate (y2,z2) for a given sensor/pixel may be determined as:

$$z2 = l^* \sin(\alpha) \quad (1)$$

$$y2 = y1 + l^* \cos(\alpha) \quad (2)$$

where l is the penetration length indicating the length from where the X-ray beam enters and leaves the food object, i.e. enters it at (y2,z2) and leaves it at (y1,0), and □ is the angular position of this given sensor in relation to the X-ray source.

This penetration length l may be based on pre-calibration where tens, hundreds, or even thousands of such or similar objects, or objects having similar material properties, are run through the X-ray and where the detected attenuation is linked to the actual penetration length of the food object. As an example, the detected attenuation value at sensor or sensor pixel may give directly the length via a kind of a lookup table.

Another alternative is to fit preferably a large number of attenuation data and perform a fitting, e.g. via polynomial formula:

$$l = A + B^* x + C^* x^2 + \quad (3)$$

which describes the penetration length of the X-rays as a function of the attenuation/pixel value p, where A, B, C, . . . , are simply the fitting parameters for this particular type of food object.

In one embodiment, the cutting process comprises cutting the food object in an angular direction in relation to the conveying direction. This greatly enhances the flexibility of the at least one subsequent processing step which does not only include e.g. cutting into portions but also includes at least partly following in the direction parallel to the conveying direction. This may e.g. be of relevance when processing fish fillets or e.g. poultry breasts, where the at least one subsequent processing step may involve such cuts. If the food object is e.g. a fish fillet, such cutting may involve cutting between the pin bones or pin bone areas, the loin part and the belly part. Subsequently, the loin and/or the belly parts may e.g. be cut into portions of e.g. fixed weight.

In the embodiments where the at least one subsequent processing step includes cutting, the cutting may be done using e.g. high pressurized water cutter, high pressurized air cutter, any type of a cutting blade and the like.

In a second aspect, the present invention relations to an apparatus comprising a X-ray device including an X-ray source, and a cutting device operable connected to a control unit to perform the above mentioned method steps.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
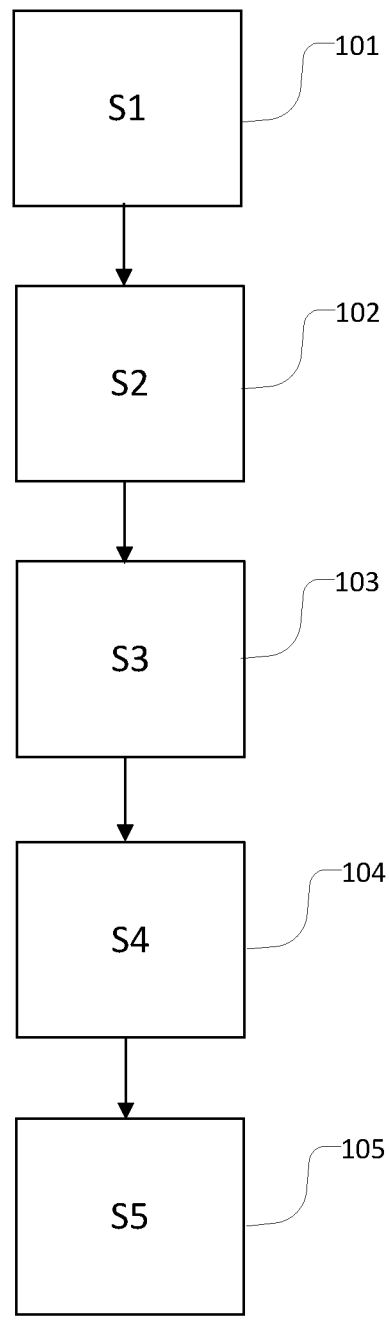
FIG. 1 shows a flowchart of a method according to the present invention of generating a three dimensional surface profile a food object.

FIG. 1 shows a flowchart of a method according to the present invention of generating a three dimensional surface profile a food object. The food object may be selected from, but is not limited to, a fish fillet, poultry breast, any type of meat, or any type of processed meat that is essentially homogeneous, typically having density close to 1. Thus, the term "penetration length" may thus be understood or be equivalent to density, and thus the term 3D surface profile may according to the present invention also be understood or be equivalent as a 3D density profile. For simplicity, in the following the term penetration length will be used and the term 3D surface profile.

In step (S1) 101, the food object is exposed with a conical X-ray beam while the food object is conveyed by e.g. any type of a conveyor comprising e.g. an endless belt on which the food item is resting while being conveyed.

In step (S2) 102, the attenuation of the X-rays after penetrating through the food object is detected using a plurality of sensors arranged below the food object, or in case mentioned above, below the conveyor belt. The plurality of sensors may in one embodiment comprise sensors are arranged in at least one line perpendicular to a conveying direction of the food item, e.g. a single line of sensors, or two or more lines of sensors that form an X-ray detection array of sensors.

In step (S3) 103, for each of the plurality of sensors, the detected intensity is converted into a penetration length, which indicates the length from where the X-ray beam enters and leaves the food object. This may be done in accordance to a pre-calibration where the different food objects of preferably identical type are run through, and where the intensities are registered and linked to the actual weight of the food objects. This may of course also be done using a material having similar material properties as the food object. Another alternative could be a fitting process that uses known weights of several food objects to obtain a formula which converts attenuation to penetration length.

As will be discussed in more details later, a data fitting process may also be applied for linking the detected attenuation values at the sensors to the actual thickness or weight of the food object.

In step (S4) 104, the surface coordinates are sequentially determined using the penetration lengths and the sensor positions as input data, and where the plurality of such surface coordinates defines the three dimensional profile. As an example, the three dimensional surface profile may be based on plurality of two dimensional surface profiles accumulated together. Such a three dimensional surface profile serves as an important input for one or more subsequent processing step such as when cutting the food object into smaller items, e.g. fixed portions fulfilling e.g. a weight and thickness criteria, where the assumption is made that the food object in homogeneous having essentially constant density.

In step (S5) 105, the detected attenuation of the X-rays after penetrating through the food object is further used for detecting undesired object or bones. This may be utilized as input data, in addition to the three dimensional surface profile, in operating for the cutting process. The cutting process may accordingly include e.g. cutting around bones, cartilages, or any type of undesired object, based on this X-ray data, and also include e.g. cutting into portions by e.g. weight using the three dimensional surface profile which may be coupled with calibrated product density. Based on the above, if the cutting tool being used is e.g. a high pressure water jet, or similar device, the cutting process may not only involve cutting perpendicular to the conveying direction when cutting into portions, but also cutting along the food object to e.g. separate meat from bones. This could e.g. be the case if the food object is a fish fillet where the cutting process includes cutting along/around the bone structure in the fish fillet.

Figure 2:
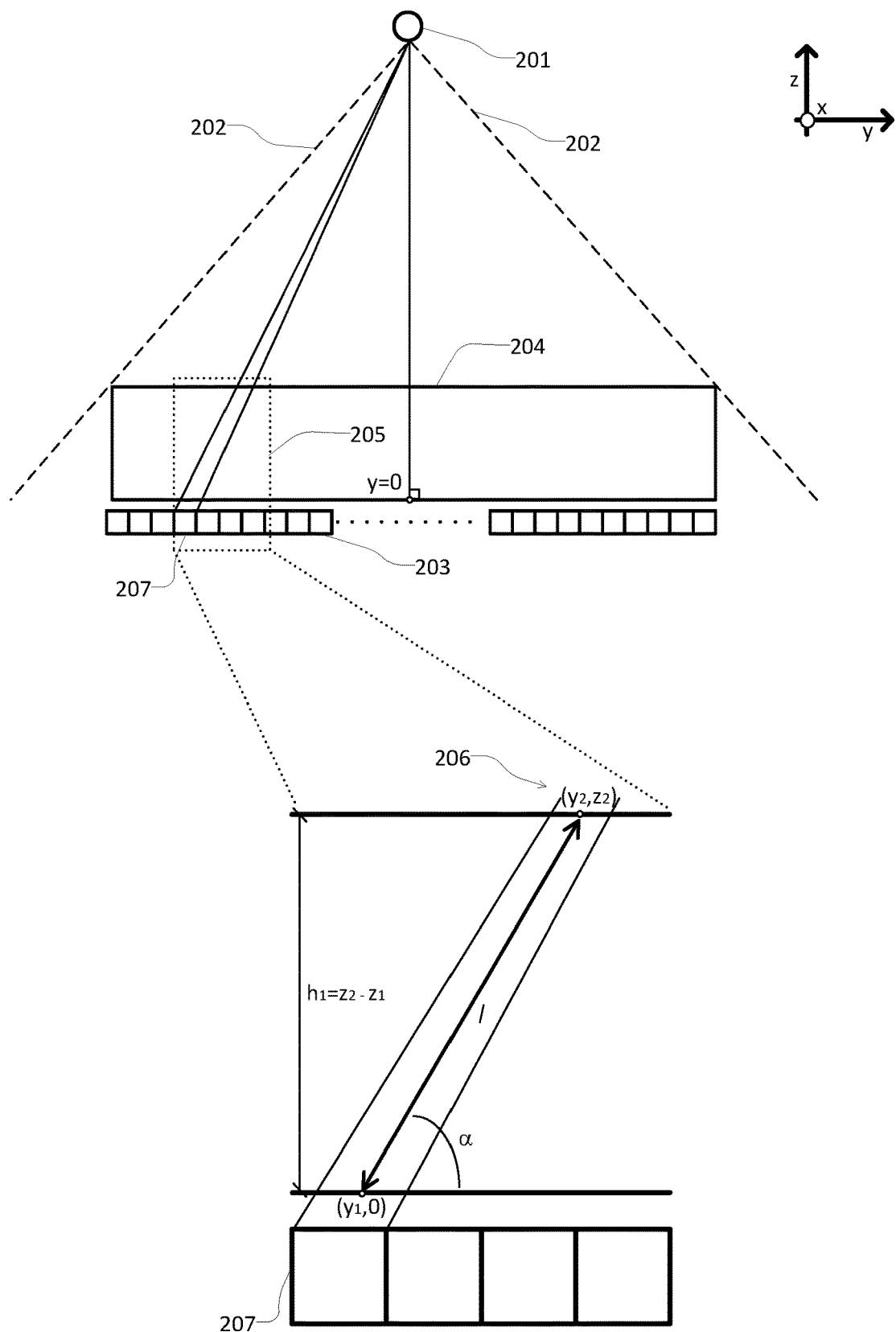
FIG. 2 depicts graphically an exemplary embodiment of how to calculate the surface coordinates discussed in relation to FIG. 1.

FIG. 2 depicts graphically an exemplary embodiment of how to calculate the surface coordinates discussed in relation to FIG. 1, using the penetration lengths and the angular positions as input data.

As shown in this front view scenario, a point like X-ray source 201 exposes a food object 204 with a X-ray beam 202 that by it's nature is conical shaped, while the food object is conveyed by a conveyor means in the x-direction as indicated by the coordinate system. The X-rays passing through the food object are detected by a plurality of sensors 203, which are arranged in at least one line perpendicular to the conveying direction of the food item. Each of the sensors may be referred to as a pixel, where the resulting attenuation values may be referred to as pixel values.

For simplicity, the food object is shown here has a rectangular front view, but obviously it can have any type of shape. The zoomed up view within the dotted lines box 205 shown below in FIG. 2 illustrates an example of how to calculate a surface coordinate (y2,z2) for a given sensor/pixel, or:

$$z2 = l*\sin(\alpha) \quad (1)$$

$$y2 = y1 + l*\cos(\alpha) \quad (2)$$

where l is the penetration length indicating the length from where the X-ray beam enters and leaves the food object, i.e. enters it at (y2,z2) and leaves it at (y1,0), and □ is the angular position of this given sensor 207 in relation to the X-ray source 201. This penetration length l may be based on pre-calibration where tens, hundreds, or even thousands of such or similar objects, or objects having similar material properties, are run through the X-ray and where the detected attenuation is linked to the actual penetration length of the food object. As an example, the detected attenuation value at sensor or sensor pixel 207 may give directly the length via a kind of a lookup table.

Another alternative is to fit preferably a large number of attenuation data and perform a fitting, e.g. via polynomial formula:

$$l = A + B*x + C*x^2 + \quad (3)$$

which describes the penetration length of the X-rays as a function of the attenuation/pixel value p, where A, B, C, . . . , are simply the fitting parameters for this particular type of food object.

The above mentioned information/calculations may also be used to determine the weight of the food object by means of correcting the attenuation of the cone shaped X-rays such that the attenuation corresponds to a vertical attenuation through the object, e.g. such that instead of the l (length between (y1,0) and (y2,z2)), that the length h1=z2−z1 is utilized as input is estimating the weight of the food object. Thus, the error caused due to the cone shape X-ray beam may be corrected.

Figure 3:
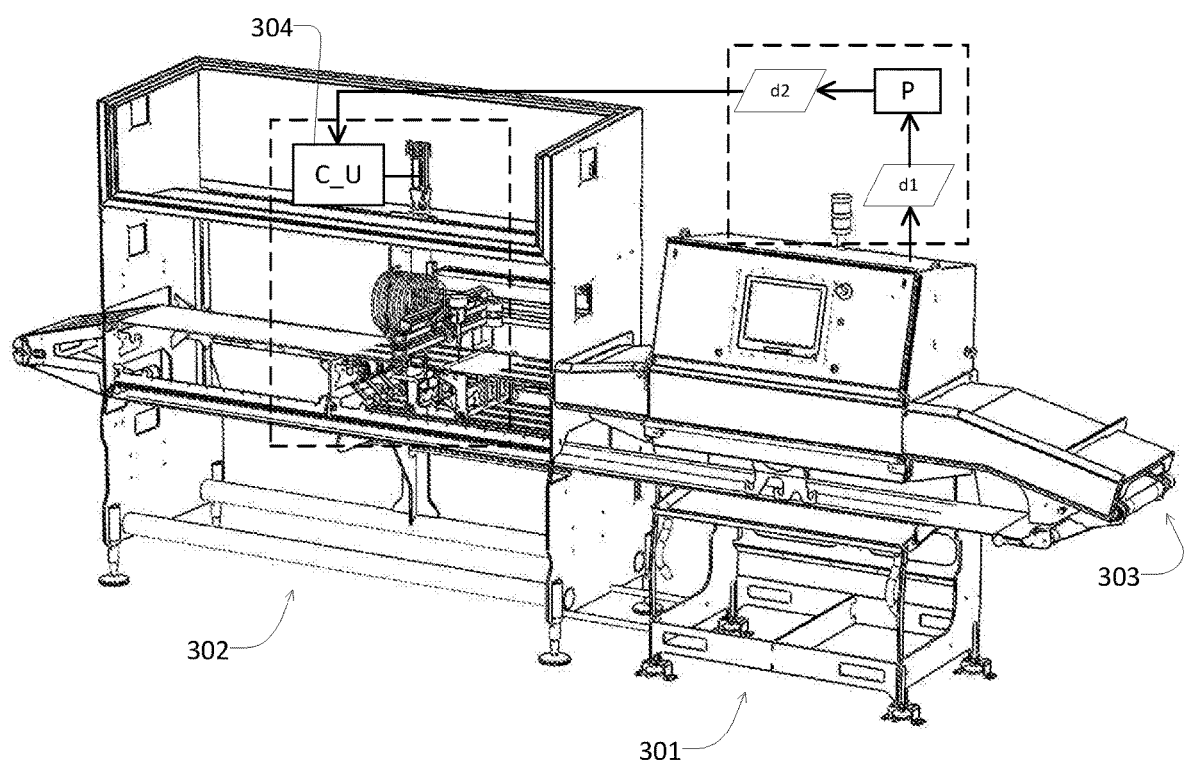
FIG. 3 depicts an example of a X-ray apparatus utilizing the method in FIG. 1.

FIG. 3 shows an embodiment of an apparatus according to the present invention for processing food objects such as fish fillets using the method discussed in relation to FIGS. 1 and 2. Such an apparatus is divided into an X-ray device 301, where the food objects are fed into the X-ray device at an in-feed end 303 where the food objects are exposed with X-rays and where the attenuation values of the X-rays are detected and processed as discussed in relation to FIGS. 1 and 2.

The figure also shows a cutting device 302 which may comprise a high pressurized water jet cutter, or similar cutting tool, operated by a control unit 304 in response to the three dimensional surface profile and eventually also additional data of the X-ray indicating e.g. the location of bones, and any type of undesired objects.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A method of generating a three dimensional surface profile of a food object, comprising:
   exposing the food object with a conical X-ray beam while the food object is conveyed,
   detecting the attenuation of the X-rays after penetrating through the food object, the detection being performed using a plurality of sensors arranged below the food object, the plurality of sensors being positioned at a pre-determined positions in relation to an X-ray source,
   converting, for each of the plurality of sensors, the detected attenuation into a penetration length of the X-ray beam, the penetration length indicating the length from where the X-ray beam enters and leaves the food object, and
   sequentially determining surface coordinates using the penetration lengths and the sensor positions as input data for making a correction of the detected attenuation of cone shaped X-rays such that the detected attenuation corresponds to a vertical attenuation through the food object.

2. The method according to claim 1, wherein the step of converting the detected attenuation into the penetration length is performed in accordance to a pre-calibration.

3. The method according to claim 1, wherein the plurality of sensors are arranged in at least one line substantially perpendicular to a conveying direction of the food object.

4. The method according to claim 3, wherein the step of sequentially determining surface coordinates comprises determining a plurality of two dimensional surface profiles, said three dimensional surface profile comprising plurality of such two dimensional surface profiles.

5. The method according to claim 1, wherein the at least one subsequent processing step comprises a cutting step.

6. The method according to claim 5, where the cutting step comprises cutting the food object into smaller portions fulfilling at least one target criterion selected from a weight target or thickness target.

7. The method according to claim 5, where the cutting process comprises cutting the food object in an angular direction in relation to the conveying direction.

8. The method according to claim 1, further comprising processing the detected attenuation of the X-rays after penetrating through the food object for detecting undesired object or bones, and where the at least one subsequent processing step comprises a cutting process performed in accordance to the detected undesired object or bones.

9. The method according to claim 8, wherein the detected undesired objects or bones is further used in operating the angle of the cutting in the food object.

10. The method according to claim 8, wherein the food object is a fish fillet and where the detected bones comprise the bone structure of the fish fillet, and where the cutting process comprises cutting around the bone structure.

* * * * *

UNITED STATES PATENT AND TRADEMARK OFFICE
CERTIFICATE OF CORRECTION

PATENT NO. : 10,845,615 B2
APPLICATION NO. : 16/337553
DATED : November 24, 2020
INVENTOR(S) : Tómas Thorsteinsson It is certified that error appears in the above-identified patent and that said Letters Patent is hereby corrected as shown below:

In the Specification

Column 1
Line 17, change "impinge" to –impinged–
Line 32, change "in less" to –in a less–
Line 47, change "may an" to –may be an–
Line 65, change "positions" to –position–

Column 2
Line 22, change "are" to –is–
Line 31, change "positions" to –position–
Line 33, change "positions" to –position–
Line 35, delete "that"
Line 41, change "step" to –step(s)–
Line 51, change "to" to –with–
Line 58, change "increase" to –increasing–

Column 3
Line 19, change "for preferably" to –for a preferably–
Line 33, change "on plurality" to –on the plurality–
Line 36, change "204 it's" to –204's–
Line 48, change "□" to –α–

Column 4
Line 19, change "relations" to –relates–
Line 21, change "operable" to –operably–
Line 37, change "profile a" to –profile of a–
Line 41, change "a" to –an–
Line 48, change "profile a" to –profile of a–
Lines 64-65, change "in case" to –in the case–

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,845,615 B2

Line 67, delete "are"

Column 5
Line 8, change "to" to –with–
Line 25, change "on plurality" to –on a plurality–
Line 28, change "step" to –steps–
Line 31, change "in" to –is–
Line 35, change "detecting undesired" to –detecting the undesired–
Line 57, change "it's" to –its–
Line 65, change "is" to –as–

Column 6
Line 10, change "□" to –α–
Line 36, change "is" to –in–

Column 8
Line 4, change "comprising plurality" to –comprising a plurality–
Line 17, change "detecting undesired" to –detecting the undesired–